United States Patent [19]

Luebbe et al.

[11] Patent Number: 4,816,261

[45] Date of Patent: Mar. 28, 1989

[54] DEODORANT GEL STICK

[75] Inventors: John P. Luebbe, Lawrenceburg, Ind.; Paul R. Tanner, Cincinnati; John D. Melanson, Jr., Fairfield, both of Ohio

[73] Assignee: The Procter & Gamble Company, Cincinnati, Ohio

[21] Appl. No.: 123,090

[22] Filed: Nov. 20, 1987

[51] Int. Cl.$^4$ .................. A61K 7/32; A61K 7/34; A61K 7/36; A61K 7/38

[52] U.S. Cl. ................. 424/65; 424/DIG. 5; 424/66; 424/67; 424/68

[58] Field of Search .............. 424/DIG. 5, 68, 66, 424/67

[56] References Cited

U.S. PATENT DOCUMENTS

| | | | |
|---|---|---|---|
| 3,255,082 | 6/1966 | Barton | 424/DIG. 5 |
| 4,126,679 | 11/1978 | Davy et al. | 424/DIG. 5 |
| 4,137,306 | 1/1979 | Rubino et al. | 424/DIG. 5 |
| 4,346,079 | 8/1982 | Roehl | 424/DIG. 5 |
| 4,720,381 | 1/1988 | Schamper et al. | 424/68 |
| 4,722,835 | 2/1988 | Schamper et al. | 424/68 |

*Primary Examiner*—Dale R. Ore
*Attorney, Agent, or Firm*—David K. Dabbiere; Steven J. Goldstein; Douglas C. Mohl

[57] ABSTRACT

Disclosed are deodorant gel stick compositions comprising from about 0.1 to about 10.0% of a deodorant active, from about 7% to about 35% of intermediate polarity emollients, from about 2% to about 8% of a benzylidene sorbitol, from about 7% to about 75% of a polar solvent, and from about 5% to about 40% of a coupling agent. These deodorant gel sticks provide very stable deodorant compositions with good efficacy as well as excellent cosmetics which are further characterized by their ease of manufacture.

16 Claims, No Drawings

DEODORANT GEL STICK

BACKGROUND OF THE INVENTION

The present invention relates to stick-type deodorant compositions. More particularly it relates to improved gel-type deodorant sticks, and also to methods for treating or preventing malodor associated with human underarm perspiration.

There are three main types of such stick formulations: compressed powder sticks, gel sticks, and wax sticks. While each of these formulation types may have advantages in certain use situations, each also has disadvantages. For example, compressed powder sticks are often brittle and hard, and leave a cosmetically-unacceptable dust upon application. Wax-based formulations can also yield cosmetically-unacceptable products due to such factors such as hardness, greasiness, and stickiness. The opacity of such wax sticks, and the residue created in their use, may also be aesthetically undesirable.

Gel based sticks have several advantages over both compressed power and wax sticks such as leaving little or no residue or dust. Gel sticks also provide a vehicle which glides easily over the skin surface.

In general soap-based gel-based sticks contain sodium stearate along with relatively high levels of either propylene glycol or ethanol. References disclosing such soap-type gel sticks include U.S. Pat. No. 4,154,816 to Roehl et al., issued May 15, 1979; U.S. Pat. No. 4,226,889 to Yukas, issued Oct. 2, 1980; and U.S. Pat. No. 4,268,498 to Gedeon et al., issued May 19, 1981.

Such soap-based sticks which contain high levels of propylene glycol tend to be sticky both during and after application thereby impartively relatively poor cosmetics. Other soap-based sticks may contain high levels of ethanol which leads to skin irritation. High lvels of ethanol also leaads to shrinkage and also weight loss of the packaged deodorant gel stick due to the volatility of ethanol.

Many stick formulations have been described in the literature which attempt to maintain the desirable cosmetic and aesthetic attributes of gel sticks, while minimizing their disadvantages. For example, antiperspirant gel sticks, using dibenzaldehyde monosorbitol acetal (herein "DBMSA") as a gelling agent, are described in U.S. Pat. No. B 4,154,816, Roehl, et al., issued May 15, 1979, U.S. Pat. No. 4,346,079, Roehl, et al., issued Aug. 24, 1982, and U.S. Pat. No. 4,518,582, Schamper, et al., issued May 21, 1985. Deodorant sticks using DMBSA are described in Japanese Patent No. 50/52,007, published Apr. 8, 1975. Nevertheless, it has been found that such DBMSA sticks, while avoiding the use of soaps, may produce products with aesthetically unacceptable stickiness. The solid gel sticks of the present invention provide very stable deodorant gel stick compositions with good efficacy as well as excellent cosmetics and aesthetics which are further characterized by their ease of manufacture.

It is therefore an object of the present invention to provide deodorant gel sticks which have good deodorant efficacy as well as improved cosmetics. It is still a further object to provide optically clear or translucent gel sticks which are cosmetically acceptable. A still further object of the present invention is to provide gel sticks which are stable and easy to formulate and manufacture. A still further object is to provide gel sticks which are non-sticky. A still further object is to provide gel sticks which contain relatively low levels of ethanol and propylene glycol to minimize skin irritation, stinging and burning.

These and other objects of the present invention will become readily apparent from the detailed description which follows.

All percentages and ratios used herein are by weight unless otherwise specified.

SUMMARY OF THE INVENTION

These gel sticks comprise:
(a) from about 0.1% to about 10% of a deodorant active;
(b) from about 7% to about 70% of an intermediate polarity emollient;
(c) from about 2% to about 8% of a benzylidene sorbitol;
(d) from about 5% to about 75% of polar solvent; and
(e) from about 5% to about 40% of a coupling agent.

These gel stick compositions have good deodorant efficacy as well as excellent cosmetics and aesthetics.

DETAILED DESCRIPTION OF THE INVENTION

Deodorant Active

Suitable deodorants include bacteriostatic quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichlorio-2'-hydroxy diphenyl ether, and zinc salts such as zinc citrate, zinc salicylate, and mixtures thereof. The preferred deodorant material is 2,4,4'-trichloro-2'-hydroxydiphenyl ether. These deodorants comprise from about 0.1% to about 10.0% of the composition.

Intermediate Polarity Emollients

The compositions of the present invention contain from about 7% to about 70% of one or more intermediate polarity emollient. Useful intermediate polariety emollients include the ethyl, isopropyl and n-butyl diesters of adipic, phthalic and sebacic acids. Preferred intermediate polarity emollients of the present invention include di-n-butyl phthalate, diethyl sebacate, diisopropyl adipate and ethyl ethyl carbomethyl phthalate, all of which are disclosed in U.S. Pat. No. 4,045,548 to Luedders et al, issued Aug. 30, 1977, which is incorporated by reference herein. The most preferred intermediate polarity emollient is di-isopropyl adipate.

Emollients among those useful herein are described in 1 *Cosmetics, Science and Technology* 27–104 (M. Balsam and E. Sagarin, Ed.; 1972), and U.S. Pat. No. 4,202,879, to Shelton, issued May 13, 1980 (both incorporated by reference herein).

The compositions of the present invention can further comprise from about 1% to about 40%, preferably from about 4% to about 20% of optional non-polar emollients. Useful non-polar emollients also include volatile silicone oils, non-polar non-volatile emollients, and mixtures thereof. The term "volatile", as used herein, refers to those materials which have a measurable vapor pressure at ambient temperature.

Volatile silicone oils useful in the cosmetic stick compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the cosmetic stick compositions disclosed herein:

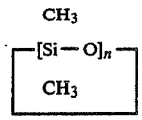

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes a 25° C. while cyclic materials typically have viscosities of less than about 10 centistokes. A description of various volatile silicone oils is found in Todd, et al., "Volatile Silicone Fluids for Cosmetics", Cosmetic & Toiletries, 91, pages 27-32 (1976), the disclosures of which are incorporated by reference herein in their entirety.

Examples of preferred volatile silicone oils useful herein include: Dow Corning 344, Dow Corning 345, and Dow Corning 200 (manufactured by the Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

Non-volatile silicone oils useful as an emollient material include polyalkylsiloxanes, polyalkylsiloxanes, and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosites from about 2 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

Benzylidene Sorbitol

The compositions of this invention also include from about 2% to about 8%, preferably from about 4% to about 6% of a benzylidene sorbitol, which serves as a gelling agent for the deodorant stick. The level of these agents are chosen so as to provide the appropriate stick hardness and the appropriate level of product transfer to the skin upon application. Such materials are generally disclosed in British Patent Specification No. 1,291,819, published Oct. 4, 1972 and in U.S. Pat. No. 4,518,582 to Schamper et al., issued May 28, 1985, both of which are incorporated by reference herein.

A preferred benzylidene sorbitol for use in the present compositions is dibenzylidene monosorbitol acetal (DMBSA). This material is commercially available, such as Gell-All-D (manufactured by New Japan Chemical Co., Ltd.) and Millithix 925 (manufactured by Milliken Chemical, Division of Milliken & Company).

Polar Solvent

The polar solvent comprises from about 7% to about 75%, preferably from about 50% to about 70% of the total composition. Useful polar solvents include propylene carbonate, water, methanol, ethanol, n-propanol, n-butanol, 2-methoxyethanol, 2-ethoxyethanol; ethylene glycol, 1,2-propylene glycol, 1,3-propylene glycol, 1,4-butylene glycol, 1,2-butylene glycol, diethylene glycol, isopropanol, isobutanol, diethylene glycol monomethylether, diethylene glycol monoethyl ether, 1,3-butylene glycol, 2,3-butylene glycol, dipropylene glycol, 2,4-dihydroxy-2-methylpentane, and the like and mixtures thereof.

These solvents are fully described in the above-referenced U.S. Pat. No. 4,518,582 to Schamper et al., issued May 21, 1985. The preferred polar solvents are propylene carbonate, ethanol, propylene glycol, 1,3-butylene glycol and 2,4-dihydroxy-2-methylpentane (sometimes referred to as hexylene glycol) and mixtures thereof. Even more preferred solvents are propylene carbonate (2-10% preferred), ethanol (15-25% preferred), propylene glycol (2-10% preferred) and dipropylene glycol (20-40% preferred).

Coupling Agents

The compositions of the present invention also essentially comprise at least one coupling agent. The term "coupling agent", as used herein, means any compound, composition, or combination thereof which acts to bring the polar, intermediate polarity and non-polar components of the present invention into a homogeneous stick composition. Preferred coupling agents for use herein are polypropylene glycol ("PPG") ethers of $C_4$-$C_{22}$ (preferably $C_{10}$-$C_{20}$) fatty alcohols. Examples of such materials are: PPG-5-ceteth-20, PPG-4 myristyl ether, PPG-4 lauryl ether, PPG-10 cetyl ether, PPG-3 myristyl ether, and mixtures thereof. Additional examples are found in CTFA Cosmetic Ingredient Dictionary. Third Edition (Estrin et al., Editors; The Cosmetic, Toiletry and Fragrance Association, Inc.; 1982), pages 252-260 and 494-500, the disclosures of which are incorporated herein by reference in their entirety.

Other useful coupling agents include $C_6$-$C_{22}$ fatty alcohols, ethoxylated derivatives of $C_4$-$C_{22}$ fatty alcohols, propoxylated derivatives of $C_4$-$C_{22}$ fatty alcohols, polyethylene glycols with a molecular weight of less than about 400, dimethyl isosorbide and mixtures thereof as described, for example, in Drug & Cosmetic Industry, 138 (2), p. 40 (1986), the disclosure of which is incorporated herein by reference. More preferred are ethoxylated derivatives of $C_{10}$-$C_{20}$ fatty alcohols, propylated derivatives of $C_{10}$-$C_{20}$ fatty alcohols, and mixtures thereof.

The coupling agent typically comprises from about 5% to about 40%, preferably from about 10% to about 30%, and most preferably from about 15% to about 25%, of the compositions of the present invention.

Optional Components

The compositions of this invention can also contain optional components which modify the physical characteristics of the gel sticks. Such components include hardeners, strengtheners, colorants, perfumes, emulsifiers, and fillers. Optional components, useful herein, are disclosed in the following patent documents, all incorporated by reference herein: U.S. Pat. No. 3,255,082, Barton, issued June 7, 1966; U.S. Pat. No. 4,137,306, Rubino, et al., issued Jan. 30, 1979; U.S. Pat. No. 4,279,658, Hooper, et al., issued July 14, 1981; and European Patent Specification No. 117,070, May, published Aug. 29, 1984.

The instant cosmetic sticks can also contain from about 0.1% to about 10% (by weight) of an inert filler material. Suitable filler materials include talc, colloidal silica (such as Cab-O-Sil, sold by Cabot Corp.), clays (such as bentonite), and mixtures thereof. The use of such fillers as stabilizing agents in cosmetic sticks is disclosed in U.S. Pat. No. 4,126,679, Davy et al., issued Nov. 21, 1978 which is incorporated by reference herein.

The compositions of the present invention can further comprise from about 0.5% to about 10% of a buffering/pH adjustment agent. Suitable agents are generally disclosed in U.S. Pat. No. 4,346,079 to Roehl, issued Aug. 29, 1982 and in European patent application No. 175,074 of Schamper et al, published Mar. 26, 1986, both of which are incorporated by reference herein.

Suitable buffering agents include coconut monoethanolamide, sodium hydroxide, stearamide, monoethanolamide, acetamide MEA, zinc acetate, zinc stearate, aluminum oxide, calcium acetate, zinc oxide, magnesium oxide, calcium carbonate, calcium hydroxide, sodium carbonate, magnesium carbonate, zinc carbonate, butyrolactone, calcium oxide, and mixtures thereof.

Method of Manufacture

Compositions of the present invention are made by art recognized methods. For example, the components can be combined and mixed thoroughly and then heated to between approximately 170° F. (77° C.) and 300° F. (149° C.) under agitation for from about 5 to about 120 minutes. The solution is then poured into stick form.

Methods for Preventing Malodor

The present invention also provides methods for treating or preventing malodor associated with human underarm perspiration. These methods comprise applying to the skin of a human a safe and effective amount of the deodorant gel of the present invention. The term "a safe and effective amount", as used herein, is an amount which is effective in eliminating or substantially reducing malodor associated with human underarm perspiration while being safe for human use at a reasonable risk/benefit ratio.

The following examples further describe and demonstrate embodiments within the scope of the present invention. These examples are solely for the purpose of illustration and are not to be construed as limitations of the present invention as many variations are possible without departing from the spirit or scope thereof.

EXAMPLE I

A deodorant composition of the present invention is made by combining the following:

| Material | Weight % |
| --- | --- |
| 2,4,4'-Trichloro-2-Hydroxy Diphenyl ether | 0.30 |
| Propylene Glycol | 3.80 |
| Dipropylene Glycol | 32.50 |
| Propylene Carbonate | 7.70 |
| Ethanol | 20.00 |
| PPG-3 Myristyl Ether | 9.60 |
| Di-isopropyl Adipate[1] | 9.60 |
| Polyethylene Glycol-6 (PEG-6) | 9.60 |
| Fragrance | 2.00 |
| Benzylidene Sorbitol[2] | 4.90 |
| | 100% |

[1]Schercemol DIA by Scher Chemicals, Inc., Clifton, New Jersey 07012
[2]Millithix 925, manufactured by Milliken Chemical, Division of Milliken & Company The deodorant gel stick composition is prepared as follows. A premix is made by combining the 2,4,4'-trichloro-2-hydroxy diphenyl ether, propylene glycol, dipropylene glycol, propylene carbonate, ethanol, PPG-3-myristyl ether, PEG-6, di-isopropyl adipate, and benzylidene monosorbitol. These components are heated to approximately 190° F. (88° C.). Once clear, the solution is then cooled to approximately 160° F. (71° C.), at which time the fragrance is added.

A uniform deodorant gel stick forms as the composition cools to room temperature. The resulting gel stick is optically clear with excellent efficacy as well as excellent nonsticky cosmetics and aesthetics.

The deodorant composition is applied to the underarm skin of a human to effectively prevent underarm odor resulting from perspiration. The composition is relatively non-sticky and feels lubricious when applied to the skin.

EXAMPLES II–IV

These deodorant gel stick compositions are made as described above in Example I.

| Material Name | Concentration (% by weight) | | |
| --- | --- | --- | --- |
| | II | III | IV |
| Benzylidene Sorbitol | 4.00 | 5.00 | 5.00 |
| Propylene Carbonate | 2.00 | 16.00 | 2.00 |
| Propylene Glycol | 5.00 | 16.00 | 2.00 |
| Cyclomethicone | 10.00 | | |
| Di-Methyl Isosorbide | 20.00 | 16.00 | 10.00 |
| Di-Isopropyl Adipate | 57.00 | | 10.00 |
| PPG-3 Myristyl Ether | | | 10.00 |
| Ethanol | | 13.00 | 19.00 |
| Dipropylene Glycol | | 16.00 | 30.00 |
| Polyethylene Glycol | | 16.00 | 10.00 |
| Triclosan | 0.30 | 0.30 | 0.30 |
| 2,4,4'-Trichloro-2-hydroxy Diphenyl ether | 0.30 | 0.30 | 0.30 |
| Perfume/Color | qs | qs | qs |
| Totals | 100.00 | 100.00 | 100.00 |

What is claimed is:
1. A deodeorant gel stick composition which comprises:
   (a) from about 0.1% to about 10% of a deodorant active;
   (b) from about 7% to about 70% of intermediate polarity emollients selected from the group consisting of ethyl, isopropyl, and n-butyl diesters of adipic, phalic and sebacic acids, and mixtures thereof;

(c) from about 2% to about 8% of a benzylidene sorbitol;

(d) from about 5% to about 75% of a polar solvent; and (e) from about 5% to about 40% of a coupling agent selected from the group consisting of polypropylene glycol ethers of $C_4$–$C_{20}$ fatty alcohols, $C_6$–$C_{22}$ fatty alcohols, ethoxylated derivatives of $C_4$–$C_{22}$ fatty alcohols, polyethylene glycols having a molecular weight of less than about 400, dimethyl isosorbide and mixtures thereof.

2. A deodorant gel according to claim 1 wherein the deodorant active component is selected from the group consisting of cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, stearyl, trimethyl ammonium chloride, 2,4,4'-trichloro-2'-hydroxy diphenyl ether, sodium aluminum chlorohydroxy lactate, zinc salicylate, and zinc citrate.

3. A deodorant gel according to claim 2 wherein the polar solvent is selected from the group consisting of monohydric alcohols, polyhydric alcohols, propylene carbonate, propylene glycol, dipropylene glycol, water and mixtures thereof.

4. A deodorant gel according to claim 3 wherein the polar solvent is selected from the group consisting of propylene carbonate, water, methanol, ethanol, n-propanol, n-butanol, 2-methoxyethanol, 2-ethoxyethanol, ethylene glycol, 1,2-propylene glycol, 1,3-propylene glycol, 1,4-butylene glycol, 1,2-butylene glycol, diethylene glycol, isopropanol, isobutanol, monomethyl ether, diethylene glycol monoethyl ether, 1,3-butylene glycol, 2,3-butylene glycol, dipropylene glycol, 2,4-dihydroxy-2-methylpentane, and mixtures thereof.

5. A deodorant gel according to claim 4 wherein the intermediate polarity emollient is selected from the group consisting of di-isopropyl adipate, di-n-butyl phtalate, diethyl sebacate, and ethyl ethyl carbomethyl phthalate, and mixtures thereof.

6. A deodorant gel according to claim 5 wherein the coupling agent is selected from the group of PPG-3 myristyl ether, polyethylene glycol with a molecular weight of less than about 400, polypropylene glycols and mixtures thereof.

7. A deodorant gel according to claim 6 wherein the polar solvent comprises components selected from the group consisting of propylene carbonate present at from about 2% to about 10% of the gel composition, ethanol present at from about 15% to about 25% of the gel composition, propylene glycol present at from about 2% to about 10% of the gel composition, dipropylene glycol present at from about 20% to about 40% of the gel composition, and mixtures thereof.

8. A deodorant gel according to claim 7 wherein the benzylidene sorbitol is dibenzyl monosorbitol acetal.

9. A deodorant gel according to claim 8, which further comprises from 1% to 40% of a non-polar emollient.

10. A deodorant gel according to claim 9 wherein the non-polar emollient is selected from the group consisting of non-polar fatty acids, fatty alcohol esters, hydrocarbons, volatile and non-volatile silicones and mixtures thereof.

11. A deodorant gel according to claim 10 which further comprises from about 0.5% to about 10% of a buffering agent.

12. A deodorant gel according to claim 11 wherein the buffering agent is selected from the group consisting of sodium aluminum chlorohydroxylactate, coconut monoethanolamide, stearamide monoethanolamide and mixtures thereof.

13. A method for treating or preventing malodor associated with human underarm perspiration, said method comprising applying to the skin of a human a safe and effective amount of a deodorant gel stick composition according to claim 1.

14. A method for preventing malodor associated with human underarm perspiration, said method comprising applying to the skin of a human a safe and effective amount of a deodorant gel stick composition according to claim 4.

15. A method for treating or preventing malodor associated with human underarm perspiration, said method comprising applying to the skin of a human a safe and effective amount of a deodorant gel stick composition according to claim 9.

16. A method for treating or preventing malodor associated with human undearm perspiration, said method comprising applying to the skin of a human a safe and effective amount of a deodorant gel stick composition according to claim 11.

* * * * *